United States Patent [19]

Usvyatsov et al.

[11] 4,102,926

[45] Jul. 25, 1978

[54] METHOD FOR PRODUCING 4-NITROSODIPHENYLAMINE

[76] Inventors: Aldan Alexandrovich Usvyatsov, ulitsa Remizova, 15; Dmitry Mikhailovich Popov, ulitsa Sumskaya, 6, korpus 4, kv. 92; Alevtina Semenovna Slavnova, ulitsa Uralskaya, 6, korpus 6, kv. 64; Elena Vladimirovna Genkina, 2 Schukinsky proezd, 19, kv. 13, all of Moscow; Nikolai Mikhailovich Vdovin, ulitsa Ordzhonikidze, 5, kv. 5, Kemerovo; Mikhail Grigorievich Pleshkov, Sovetsky prospekt, 79, kv. 22, Kemerovo; Ravil Safinovich Safin, prospekt Lenina, 63, kv. 54, Kemerovo; Sergei Nikolaevich Naumov, ulitsa Vesennaya, 24, kv. 98, Kemerovo; Felix Georgievich Kokoulin, Sevastopolsky prospekt, 65/15, kv. 69, Moscow; Georgy Borisovich Manelis, ulitsa Dmitria Ulyanova, 4, korpus B, kv. 339, Moscow; Valentina Petrovna Trofilkina, ulitsa letchika Babushkina, 33, korpus 1, kv. 38, Moscow; Ljudmila Ilinichna Te, Sovetsky prospekt, 110, kv. 23, Kemerovo; Olga Nikolaevna Voronkova, Sovetsky prospekt, 87, kv. 36, Kemerovo; Galina Alexandrovna Formenova, ulitsa Vesennaya, 22, kv. 33, Kemerovo, all of U.S.S.R.

[21] Appl. No.: 757,348

[22] Filed: Jan. 6, 1977

[51] Int. Cl.² ............................................. C07C 87/60
[52] U.S. Cl. .................................................... 260/576
[58] Field of Search ................................ 260/576, 647

[56] References Cited

U.S. PATENT DOCUMENTS 2,560,893  7/1951  Roberts .............................. 260/576
3,429,924  2/1969  Ellerbrook et al. ................. 260/576
3,728,392  4/1973  Levy et al. .......................... 260/576
3,748,362  7/1973  Kinstler .............................. 260/576
3,978,131  8/1976  Pawellek et al. ................... 260/576

FOREIGN PATENT DOCUMENTS 2,211,341  9/1973  Fed. Rep. of Germany ....... 260/576
41-1,235   1/1966  Japan .................................. 260/576

OTHER PUBLICATIONS

Dost et al., "Chem. Ab.", vol. 52, Ab. No. 4686g (1958).
Martynov et al., "Chem. Ab.", vol. 80, Ab. No. 84063k (1974).

Primary Examiner—Daniel E. Wyman
Assistant Examiner—John J. Doll
Attorney, Agent, or Firm—Lackenbach, Lilling & Siegel

[57] ABSTRACT

A method for producing 4-nitrosodiphenylamine, consisting in diphenylamine nitrozation with nitrites of alkali metals or ammonium nitrite in the presence of an acid and an organic solvent nonmiscible with water; said nitrozation being carried out under stirring with a speed determined by Reynolds number not below, $8-10 \times 10^3$ or in the presence of polymers of methacrylic acid esters in an amount of 0.01–0.02% of the reaction mixture weight under stirring with a speed determined by Reynolds number equal to $4-5 \times 10^3$; this is followed by rearrangement of the resultant N-nitrosodiphenylamine with anhydrous hydrogen chloride in an inert gas atmosphere in the presence of an alkyl 4-aminodiphenylamine in an amount of 0.5–1% of the N-nitrosodiphenylamine weight, with subsequent neutralization of the formed 4-nitrosodiphenylamine hydrochloride and isolation of the desired product. The method described above makes it possible to increase the product yield at the nitrozation stage by a factor of 5–6 and to raise the yield of the desired product up to 99% in terms of the converted N-nitrosodiphenylamine. 4-Nitrosodiphenylamine produced serves as an intermediate in the synthesis of antioxidants for rubbers and plastics, in the synthesis of dyestuffs, and is also used as a component in a number of antioxidant compositions.

9 Claims, No Drawings

METHOD FOR PRODUCING 4-NITROSODIPHENYLAMINE

The present invention relates to methods for producing 4-nitrosodiphenylamine. 4-Nitrosodiphenylamine is an intermediate in the synthesis of antioxidants for rubbers and plastics, for example, an alkyl 4-aminodiphenylamine, in the synthesis of dyestuffs, and is also used as a component of a number of antioxidant compositions.

A number of methods have been known to produce 4-nitrosodiphenylamine through diphenylamine nitrosation with nitrites of alkali metals or with ammonium nitrite in the presence of an acid and an organic solvent, followed by rearrangement of the resultant N-nitrosodiphenylamine, by neutralization of the forming 4-nitrosodiphenylamine hydrochloride and by isolation of the desired product.

A disadvantage of the known methods is that diphenylamine nitrosation is carried out in the presence of an organic solvent miscible with water, N-nitrosodiphenylamine being separated from the reaction mixture as a crystalline product. Such a method for producing N-nitrosodiphenylamine is little suited in the cases when N-nitrosodiphenylamine is an intermediate for 4-nitrosodiphenylamine production. Under industrial conditions, therefore, diphenylamine nitrosation is carried out in the presence of an organic solvent nonmiscible with water, thus making it possible to avoid N-nitrosodiphenylamine separation from the reaction mixture and to transfer same to the next production stage as a solution separated from the aqueous solution of the salts by settling. Nitrosation is continuously carried out in reactors connected in series and equipped with agitators. Said process is accompanied by the formation of by-products such as diphenylamine nitroderivatives in an amount of 1-2% of diphenylamine introduced. The nitrosation process cycle ranges from 3 to 3.5 hours.

When carrying out the stage of N-nitrosodiphenylamine rearrangement into 4-nitrosodiphenylamine under industrial conditions in accordance with the prior-art methods, an essential disadvantage of said stage becomes manifest. This disadvantage is that in the course of rearrangement 4-nitrosodiphenylamine hydrochloride forms crystalline agglomerates on the reactor walls, these agglomerates become resinified and, periodically falling down from the reactor walls are carried into the neutralization and then into the separation units together with the reaction mixture, making the neutralization process difficult and causing losses of the desired product becase of indistinct stratification of the aqueous and organic phases.

In accordance with another known procedure the process of rearrangement is carried out under conditions ensuring complete dissolution of the forming 4-nitrosodiphenylamine hydrochloride. This is achieved by conducting the process at about 40° C in a methanol-benzene mixture taken in a weight ratio of 1:1.2, respectively, thereby producing 4-nitrosodiphenylamine hydrochloride solution with a concentration of about 15 wt.%, the yield of the desired product amounting to 93%. The temperature adopted for the process necessitates a sufficiently short process cycle, which can be achieved either by increasing the HCl: N-nitrosodiphenylamine molar ratio (to 4.5), or by raising N-nitrosodiphenylamine concentration in the initial reaction mixture (up to 30 wt.%) and carrying out the process with an incomplete degree of conversion (approx. 50%).

The first of said procedures leads to higher consumption of inorganic materials (HCl and NaOH), the second one necessitates recycling N-nitrosodiphenylamine solution in benzene resulting, therewith, in inevitable accumulation of by-products and resins. It has been proposed to remove the latter either through periodical renewal of the whole system, or through continuous withdrawal of a certain amount of benzene solution from the cycle. In both cases recovery of the solvent and N-nitrosodiphenylamine has been envisaged, which inevitably leads to losses of the latter, taking into account its thermal instability. Besides, said recycling complicates the process flowsheet.

It is an object of the present invention to provide a method for producing 4-nitrosodiphenylamine, which increase the yield of the desired product.

In accordance with the above-mentioned and other objects, the present invention resides in the provision of a method for producing 4-nitrosodiphenylamine through diphenylamine nitrosation with nitrites of alkali metals or ammonium nitrite in the presence of an acid and an organic solvent nonmiscible with water, followed by rearrangement of the resultant N-nitrosodiphenylamine with anhydrous hydrogen chloride, by neutralization of the formed 4-nitrosodiphenylamine hydrochloride and by isolation of the desired product. In accordance with the invention, diphenylamine nitrosation is carried out with stirring at a speed determined by a Reynolds number not below $8-10\times10^3$, or in the presence of polymers of methacrylic acid esters in an amount of 0.01-0.02% of the reaction mixture weight under stirring with a speed determined by a Reynolds number equal to $4-5\times10^3$, N-nitrosodiphenylamine rearrangement being is carried out in an inert gas atmosphere in the presence of alkyl 4-aminodiphenylamine in an amount of 0.5-1% of the N-nitrosodiphenylamine by weight.

Nitrosation carried out under the conditions specified in the present invention permits the product yield to be raised by a factor of 5-6 per unit of the reactor volume and the amount of by-products to be decreased from 1-2 to 0.4-1.0% in terms of converted diphenylamine.

The conditions under which the rearrangement stage is conducted make it possible to eliminate oxidation of NO evolving during the process to $NO_2$, thus ruling out the possibility of side reactions. The latter circumstance combined with the presence of an alkyl 4-aminodiphenylamine in the system, results in obtaining a reaction mixture which is a fine disperse suspension of 4-nitrosodiphenylamine hydrochloride in an organic solvent (particle size: 0.2-0.6 mm).

No crystalline agglomerates are formed in said suspension and deposited on the inner surface of the reactor under the process conditions, thus resulting in smaller amounts of by-products and resins formed.

By virtue of fine disperse suspension of hydrochloride being fed to the neutralization stage the process cycle can be cut down (from 1 hour to 15-25 min), separation conditions of the organic and aqueous phases can be improved, and the yield of the desired product can be raised to 98-99% in terms of converted N-nitrosodiphenylamine.

The herein-proposed method for producing 4-nitrosodiphenylamine can be realized both as a batch and as a continuous process preferably, in the following way.

Initial diphenylamine solution in an organic solvent nonmiscible with water, an aqueous solution of an alkali metal nitrite or ammonium nitrite, and an acid are simultaneously fed into a nitrosation reactor equipped with a cooling jacket and an agitator ensuring the required intensity of stirring. Nitrosation process cycle for the batch process ranges from 15 to 20 minutes, and amounts to 1 hour in the case of the continuous process. The process temperature ranges from 17° to 20° C. On completion of nitrosation the reaction mixture is separated into aqueous and organic phases. The latter, being N-nitrosodiphenylamine solution, is fed to the rearrangement stage. The aqueous phase is discharged as a water-salt industrial waste after excess acid has been neutralized.

Trichloroethylene, chlorobenzene, benzene, toluene and other available organic solvents nonmiscible with water, not interacting with the nitrosation process reaction mixture components and suitable for the subsequent production stage-N-nitrosodiphenylamine rearrangement into 4-nitrosodiphenylamine can be used as an organic solvent.

Available mineral acids such as $H_2SO_4$ or HCl are preferable for carrying out nitrosation; however, other acids, such as acetic acid, can also be used.

N-nitrosodiphenylamine solution in an organic solvent, obtained at the nitrosation stage, is fed into a rearrangement reactor (or into a group of reactors connected in series when carrying out the continuous process) equipped with an agitator and a cooling jacket, and connected with a system making it possible to establish an inert gas atmosphere in the reactor using nitrogen, for example. An alkyl 4-aminodiphenylamine solution in the same organic solvent as for N-nitrosodiphenylamine, and anhydrous hydrogen chloride are fed into the reactor along with N-nitrosodiphenylamine solution. The rearrangement process is carried out with stirring for about 4.5–5 hours at 15°–25° C.

The resultant fine disperse suspension of 4-nitrosodiphenylamine hydrochloride in the organic solvent is fed into a neutralizer prefilled with a neutralizing agent and equipped with an agitator and a cooling jacket. Crystalline 4-nitrosodiphenylamine is separated from the reaction mixture by filtration on completion of the neutralization process, whereas the mother liquor is separated, by settling, into aqueous and organic phases, the latter being an initial organic solvent, containing unconverted N-nitrosodiphenylamine and resinification products. The solvent is regenerated by distillation and recycled to the diphenylamine initial solution preparation stage. The aqueous phase containing alkali metal chloride or ammonium chloride and the unreacted neutralizing agent, is discharged as an industrial waste.

4-Nitrosodiphenylamine separated by filtration is washed with water and dried in air.

When using 4-nitrosodiphenylamine as an intermediate in the production of alkyl 4-aminodiphenylamines, neutralization can be carried out in excess alkali metal hydroxide for producing a 4-nitrosodiphenylamine aqueous-alkaline salt solution which is conveyed to the next production stage without separating free 4-nitrosodiphenylamine. The present invention will be better understood from a consideration of the following examples illustrating the proposed method for producing 4-nitrosodiphenylamine.

EXAMPLE 1

210 g of 20% diphenylamine solution in trichloroethylene, 59 g of 38% sodium nitrite aqueous solution and 150 g of 20% sulfuric acid are simultaneously fed, under stirring, (Re = $8-10\times10^3$) at 17°–20° C for about 7–10 min into a 500 ml reactor equipped with a cooling jacket, a thermometer and an agitator; this is followed by another stirring for about 5–8 min. The stirring is discontinued after said period of time has elapsed; complete layer separation of the organic and aqueous phases takes place during 15–20 min. 217 g of organic phase containing 48.4 g of N-nitrosodiphenylamine and 0.42 g of diphenylamine are obtained. Diphenylamine conversion degree is 99%; N-nitrosodiphenylamine yield, 99.3% in terms of converted diphenylamine.

This solution (organic phase) is added with 0.48 g of 4-isopropylaminodiphenylamine (1% of N-nitrosodiphenylamine weight) and then poured into a 300 ml rearrangement reactor equipped with a lock agitator, a thermometer, a cooling jacket, a dropping funnel and a drain cock. The reactor is purged with nitrogen; 27.2 g of methanol containing 12.2 g of anhydrous hydrogen chloride (1.37 mole per mole of N-nitrosodiphenylamine) are poured into the dropping funnel, and then fed into the reactor during 15–20 min with stirring, the temperature being maintained not above 20°.

The reaction mixture is kept and stirred at said temperature for 4.5–5 hours. The resulting suspension of 4-nitrosodiphenylamine hydrochloride is of brick-red color with the particle size ranging from 0.2 to 0.6 mm. Through the drain cock of the rearrangement reactor the suspension is fed into a 450 ml neutralizer equipped with an agitator, a thermometer, a cooling jacket and a drain cock. 73 g of 20% NaOH aqueous solution are fed into the neutralizer prior to feeding the suspension. The suspension is fed into the neutralizer with the agitator working during 10 minutes at 20°–25° C, kept at this temperature for 5–10 min; then the stirring is discontinued and the neutralizer contents are delivered to filtration through the drain cock. The mother liquor is separated by settling into aqueous and organic phases.

The latter is an organic solvent containing unconverted N-nitrosodiphenylamine and by-products. 46.8 g of crystalline 4-nitrosodiphenylamine and 170.2 g of trichloroethylene containing 0.4 g of N-nitrosodiphenylamine are produced. N-nitrosodiphenylamine conversion degree is 99.2%; 4-nitrosodiphenylamine yield is 97.5% in terms of converted N-nitrosodiphenylamine.

EXAMPLE 2

The nitrosation process is carried out as described in Example 1. 0.04 g (0.01% of the reaction mixture weight) of polymethyl methacrylate, Re = $4-5\times10^3$, are added to diphenylamine solution in trichloroethylene. 216.5 g of organic phase containing 48.2 g of N-nitrosodiphenylamine and 0.5 g of diphenylamine are obtained. Diphenylamine conversion degree is 98.8%; N-nitrosodiphenylamine yield is 99% in terms of converted diphenylamine.

Subsequent stages of rearrangement, neutralization and isolation of the desired product are carried out as described in Example 1.

N-nitrosodiphenylamine conversion degree and the yield of 4-nitrosodiphenylamine in terms of converted N-nitrosodiphenylamine are the same as in Example 1.

EXAMPLE 3

The nitrosation process is carried out as described in Example 2.

0.06 g (0.015% of the reaction mixture weight) of polymethyl methacrylate are added to diphenylamine solution in trichloroethylene. 216.5 g of organic phase containing 48 g of N-nitrosodiphenylamine and 0.5 g of unconverted diphenylamine are obtained. Diphenylamine conversion degree is 98.8%; N-nitrosodiphenylamine yield is 98.6% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 4

The nitrosation process is carried out as described in Example 2. 0.08 g (0.02% of the reaction mixture weight) of polymethyl methacrylate are added to diphenylamine solution in trichloroethylene. 216.7 g of organic phase containing 48.4 g of N-nitrosodiphenylamine and 0.5 g of diphenylamine are obtained. Diphenylamine conversion degree is 98.8%; N-nitrosodiphenylamine yield is 99.4% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 5

The nitrosation process is carried out as described in Example 2. 0.08 g (0.02% of the reaction mixture weight) of polymethyl methacrylate are added to diphenylamine solution in trichloroethylene. 217 g of organic phase containing 48.4 g of N-nitrosodiphenylamine and 0.44 g of diphenylamine are obtained. Diphenylamine conversion degree is 98.9%; N-nitrosodiphenylamine yield is 99.3% in terms of converted diphenylamine.

Subjequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 6

The nitrosation process is carried out as described in Example 1. 210 g of 20% diphenylamine solution in toluene are fed into the reactor. 216.8 g of organic phase containing 48 g of N-nitrosodiphenylamine and 0.48 g of unconverted diphenylamine are obtained. Diphenylamine conversion degree is 98.9%; N-nitrosodiphenylamine yield is 98.5% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 7

The nitrosation process is carried out as described in Example 1. 210 g of 20% diphenylamine solution in benzene are fed into the reactor. 216.5 g of organic phase containing 47.8 g of N-nitrosodiphenylamine and 0.5 g of unconverted diphenylamine are obtained. Diphenylamine conversion degree is 98.8%; N-nitrosodiphenylamine yield is 98.2% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 8

The nitrosation process is carried out as described in Example 1. 210 g of 20% diphenylamine solution in chlorobenzene are fed into the reactor. 216.6 g of organic phase containing 47.8 g of N-nitrosodiphenylamine and 0.44 g of diphenylamine are obtained. Diphenylamine conversion degree is 98.8%; N-nitrosodiphenylamine yield is 98% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 9

The nitrosation process is carried out as described in Example 2. 210 g of 20% diphenylamine solution in toluene are fed into the reactor. 217 g of organic phase containing 48.2 g of N-nitrosodiphenylamine and 0.44 g of diphenylamine are obtained. Diphenylamine conversion degree is 99%, N-nitrosodiphenylamine yield is 98.8% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 10

The nitrosation process is carried out as described in Example 1.117 g of 10% hydrochloric acid, Re = $50 \times 10^3$, are fed into the reactor. 216.7 g of organic phase containing 47.8 g of N-nitrosodiphenylamine and 0.5 g of unconverted diphenylamine are obtained. Diphenylamine conversion degree is 98.8%; N-nitrosodiphenylamine yield is 98.2% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 11

The nitrosation process is carried out as described in Example 1. 68.6 grams of 40% potassium nitrite aqueous solution, Re = $25 \times 10^3$, are fed into the reactor. 216.8 g of organic phase containing 48.2 g of N-nitrosodiphenylamine and 0.4 g of unconverted diphenylamine are obtained. Diphenylamine conversion degree is 99%; N-nitrosodiphenylamine yield is 98.9% in terms of converted diphenylamine.

Subsequent stages of rearrangement, neutralization and isolation of the desired product are carried out as described in Example 1.

N-nitrosodiphenyldiamine conversion degree and 4-nitrosodiphenylamine yield in terms of converted N-nitrosodiphenylamine are the same as in Example 1.

EXAMPLE 12

The nitrosation process is carried out as described in Example 1. 106 grams (99.1 ml) of ammonium nitrite aqueous solution containing 200 g/l of $NH_4NO_2$, and 44.6 g of 70% sulfuric acid are fed into the reactor. 216.8 g of organic phase containing 48.2 g of N-nitrosodiphenylamine and 0.4 g of unconverted diphenylamine are obtained.

Diphenylamine conversion degree is 99%; N-nitrosodiphenylamine yield is 98.9% in terms of converted diphenylamine.

Subsequent stages of rearrangement, neutralization and isolation of the desired product are carried out as described in Example 1.

N-nitrosodiphenylamine conversion degree and 4-nitrosodiphenylamine yield in terms of converted N-nitrosodiphenylamine are the same as in Example 1.

EXAMPLE 13

The process is carried out as described in Example 1. 0.24 g of 4-isopropylaminodiphenylamine (0.5% of N-nitrosodiphenylamine weight) are fed into the rearrangement reactor. The process characteristics are the same as in Example 1.

EXAMPLE 14

The process is carried out as described in Example 1. 0.36 g of 4-isopropylaminodiphenylamine (0.75% of N-nitrosodiphenylamine weight) are fed into the rearrangement reactor. The process characteristics are the same as in Example 1.

EXAMPLE 15

The process is carried out as described in Example 1. 0.48 g of 4-isopropylaminodiphenylamine (1% of N-nitrosodiphenylamine weight) are fed into the rearrangement reactor. The process characteristics are the same as in Example 1.

EXAMPLE 16

The process is carried out as described in Example 1. 68 g of 10% aqueous ammonia solution are fed into the neutralizer. N-nitrosodiphenylamine conversion degree is 99.2%, 4-nitrosodiphenylamine yield is 99.0% in terms of converted N-nitrosodiphenylamine.

EXAMPLE 17

210 g/h of 20% diphenylamine solution in trichloroethylene, 59 g/h of 38% sodium nitrite aqueous solution and 150 g/h of 20% sulfuric acid are fed with stirring, Re = $8 \times 10 \cdot 10^3$, into a 500 ml reactor equipped with a cooling jacket, a thermometer and an agitator. The nitrosation process temperature is maintained at 17°–20° C. Residence time of the reaction mixture in the reactor is 1 h.

The reaction mixture is discharged from the reactor into a separation vessel where the aqueous and organic phases are separated within 15–20 min. The lower layer, N-nitrosodiphenylamine solution in trichloroethylene, leaves the separation vessel and enters the collection vessel, wherefrom the solution is delivered to the rearrangement stage. The top aqueous layer is discharged as a waste product after neutralization of excess sulfuric acid.

2100 g of the solution, containing 420 g of diphenylamine have been fed into the reactor within 10 hours, and 2170 g of the solution containing 482 g of N-nitrosodiphenylamine and 2.1 g of unconverted diphenylamine have been obtained. Diphenylamine conversion degree is 99%; N-nitrodiphenylamine yield is 99.3% in terms of converted diphenylamine.

4.8 g of 4-isopropylaminodiphenylamine are added to 2170 g of N-nitrosodiphenylamine solution in trichloroethylene obtained at the nitrosation stage; this solution is continuously fed at a rate of 217 g/h into the first reactor of a group of rearrangement reactors comprising four 300 ml reactors connected in series, each equipped with a lock agitator, a thermometer and a cooling jacket. These reactors are connected with a system providing an inert gas (nitrogen) atmosphere in the reactors. 27.2 g/h of methanol and 12.2 g/h of anhydrous hydrogen chloride dissolved in said methanol are fed into the first reactor simultaneously with feeding N-nitrosodiphenylamine. The process temperature is maintained at 15°–25° C; the residence time of the reaction mixture in the group of the reactors is 5 hours. On leaving the fourth reactor of the group, 4-nitrosodiphenylamine hydrochloride suspension enters a 250 ml neutralizer equipped with a lock agitator, a thermometer and a cooling jacket. Prior to feeding 4-nitrosodiphenylamine hydrochloride suspension, said neutralizer is with 72 g of 25% ammonium chloride aqueous solution containing 1.6–1.8 wt.% ammonia. Along with the suspension 70 g/h of 10% aqueous ammonia solution are fed into the neutralizer. The temperature in the neutralizer is maintained at 20.25° C.

From the neutralizer the reaction mixture is delivered to a filter on which 473.4 g of crystalline 4-nitrosodiphenylamine are separated during 10 hours; the product is washed with 500 ml of water and dried in air.

The mother liquor is separated into a water layer which is a 25% solution of ammonium chloride containing 1.6–1.8 wt.% ammonia and an organic layer which is 1692 g of trichloroethylene containing 3.8 g of N-nitrosodiphenylamine.

N-nitrosodiphenylamine conversion degree is 99.2%; 4-nitrosodiphenylamine yield reaches 99% in terms of converted N-nitrosodiphenylamine.

What is claimed is:

1. A method for producing 4-nitrosodiphenylamine, wherein diphenylamine is nitrosated with a nitrosating agent selected from the group consisting of nitrates of alkali metals and ammonium nitrite in the presence of an acid and an organic solvent immiscible with water; followed by rearrangement of the resultant N-nitrosodiphenylamine with anhydrous hydrogen chloride in an inert gas atmosphere in the presence of an alkyl 4-aminodiphenylamine in an amount of 0.5–1% of N-nitrosodiphenylamine by weight; the forming 4-nitrosodiphenylamine hydrochloride being then neutralized and the desired product isolated.

2. The method of claim 1, wherein said nitrosation is carried out under stirring at a speed determined by a Reynolds number not less than $8-10 \times 10^3$.

3. The method of claim 1, wherein said nitrosation is carried out in the presence of polymers of methacrylic acid esters in an amount of from 0.01–0.02% of the reaction mixture weight, under stirring at a speed determined by a Reynolds number equal to $4-5 \times 10^3$.

4. The method of claim 1, wherein said alkyl 4-aminodiphenylamine is 4-isopropylaminodiphenylamine.

5. The method of claim 1, wherein said inert gas atmosphere is provided by nitrogen.

6. The method of claim 1, wherein said acid is a mineral acid.

7. The method of claim 6, wherein said acid is selected from the group consisting of sulfuric acid and hydrochloric acid.

8. The method of claim 1, wherein said acid is acetic acid.

9. The method of claim 1, wherein said organic solvent is selected from the group consisting of trichloroethylene, chlorobenzene, benzene, and toluene.

* * * * *